(12) United States Patent
Chung et al.

(10) Patent No.: US 9,717,570 B2
(45) Date of Patent: Aug. 1, 2017

(54) SCAN BODY FOR A DENTAL IMPRESSION

(71) Applicants: Felix Chung, Chantilly, VA (US);
Joshua Townsend, Chantilly, VA (US)

(72) Inventors: Felix Chung, Chantilly, VA (US);
Joshua Townsend, Chantilly, VA (US)

( * ) Notice: Subject to any disclaimer, the term of this patent is extended or adjusted under 35 U.S.C. 154(b) by 0 days.

(21) Appl. No.: 14/723,387

(22) Filed: May 27, 2015

(65) Prior Publication Data
US 2016/0346065 A1 Dec. 1, 2016

(51) Int. Cl.
A61C 9/00 (2006.01)
A61C 8/00 (2006.01)

(52) U.S. Cl.
CPC ............ *A61C 8/0001* (2013.01); *A61C 9/004* (2013.01); *A61C 9/0006* (2013.01); *A61C 9/0053* (2013.01)

(58) Field of Classification Search
CPC ............................ A61C 8/0001; A61C 9/0006
See application file for complete search history.

(56) References Cited

U.S. PATENT DOCUMENTS

| | | | |
|---|---|---|---|
| 8,867,800 B2 | 10/2014 | Bullis et al. | |
| 8,882,508 B2 | 11/2014 | Bellance et al. | |
| 8,936,468 B2 | 1/2015 | Ranck et al. | |
| 2010/0159417 A1 | 6/2010 | Whipple | |
| 2014/0113252 A1* | 4/2014 | Hung | A61C 8/0025 433/201.1 |
| 2014/0178835 A1 | 6/2014 | Lin | |
| 2015/0173870 A1* | 6/2015 | Suttin | A61C 8/008 433/202.1 |
| 2016/0015488 A1* | 1/2016 | Miltau | A61C 8/0001 433/75 |

FOREIGN PATENT DOCUMENTS

KR 10-20130029848 3/2013

* cited by examiner

*Primary Examiner* — Rex R Holmes
(74) *Attorney, Agent, or Firm* — Richard C. Litman

(57) ABSTRACT

The scan body for a dental impression includes a hollow member having a mounting recess configured for mounting onto a head portion of an impression coping positioned in a dental impression. The mounting recess can have an internal threaded bore for receiving a fastener to secure the scan body onto the impression coping. The scan body can have an exterior peripheral wall extending between opposing first and second ends. The peripheral wall has a first flat surface and a second flat surface. The first flat surface and the second flat surface have different dimensions.

9 Claims, 7 Drawing Sheets

SCAN BODY FOR A DENTAL IMPRESSION

BACKGROUND OF THE INVENTION

1. Field of the Invention

The present invention relates to dental devices and, particularly, to a scan body for mating to an impression coping positioned in a dental impression.

2. Description of the Related Art

To replace a broken or damaged tooth a patient will typically undergo a surgical procedure in which a dentist places an implant in the location of the patient's mouth missing the tooth/teeth. Generally, the implant will incorporate an opening having a hexagonal shape for receiving an impression coping and, subsequently, a dental prosthesis. After the implant has been inserted into the patient's mouth, the dentist will typically insert the impression coping, having a head portion, into the implant having the opening configured for receiving the head portion of the impression coping.

Subsequently, the dentist will take a "pick-up" dental impression of the patient's mouth having the impression coping. Once the impression material has hardened and the dental impression is complete, the dentist can remove the "pick-up" dental impression from the patient's mouth and attach a female hex onto the head portion, having a hexagonal shape, of the impression coping. This can then be sent to a lab to create a dental mold, in stone form, of the patient's teeth with the female hex representing the position of the implant in the patient's mouth. It is to be noted that the "pick-up" dental impression is used only for implant cases.

A scan body is screwed into the female hex positioned inside the dental mold and the dental mold is scanned using a CADCAM computer program so as to design the prosthetic tooth virtually. The scan body can have indexing means that can allow the CADCAM program to determine the orientation and angle of the scan body relative to the hex shape on the dental mold, so that the CADCAM program can design the implant prosthetic correctly. The conventional scan body has an opening through which a screw extends. This hole causes slight distortion in the screw.

While most CADCAM scanners have the ability to scan both dental impressions and dental molds, a majority of the dentists are currently scanning the dental molds instead of using the dental impressions created directly from the patient's mouth. Relying on the dental molds, however, can negatively impact the accuracy of the design of the prosthetic tooth implanted into a patient's mouth since accuracy tends to decrease each time information is transferred from the patient's mouth to the dental impression, from the dental impression to the dental mold and from the dental mold to the scanned impression, which then must be restored in a digital format by the computer. Further, most scan bodies are too large to fit within smaller gaps between teeth.

Thus, a scan body for a dental impression solving the aforementioned problems is desired.

SUMMARY OF THE INVENTION

An embodiment of a scan body for a dental impression includes a substantially hollow member with a mounting recess defined therein for mounting onto an impression coping positioned in a dental impression. The mounting recess can have an internal threaded bore configured to receive a fastener extending through the impression coping for securing the scan body onto the impression coping. The hollow member can have an exterior peripheral wall extending between the first and second ends, the exterior wall having a first flat surface and a second flat surface, the first flat surface and the second flat surface having different dimensions.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
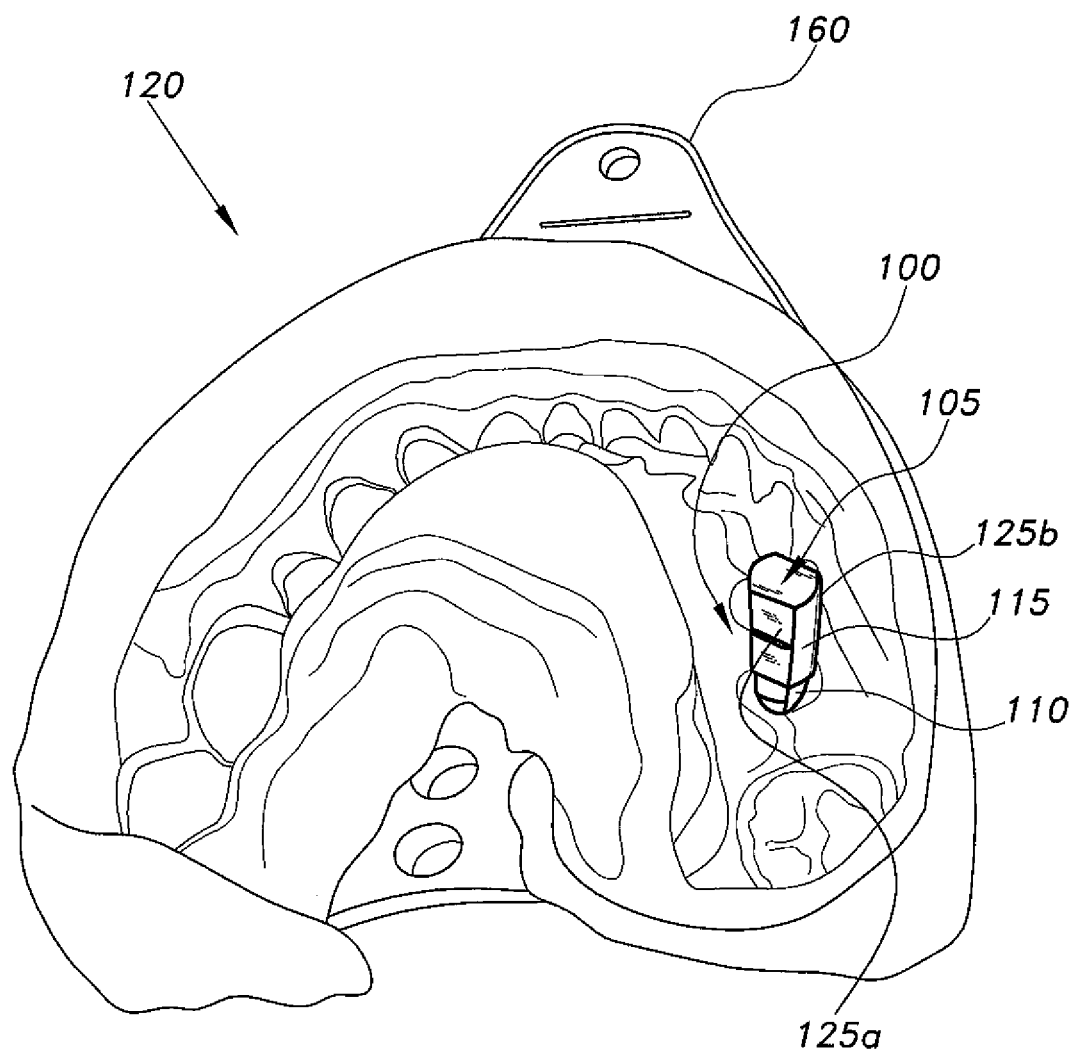
FIG. 1 is an top, rear environmental view of a scan body coupled to an impression coping positioned in a dental impression according to the present invention.
Figure 3:
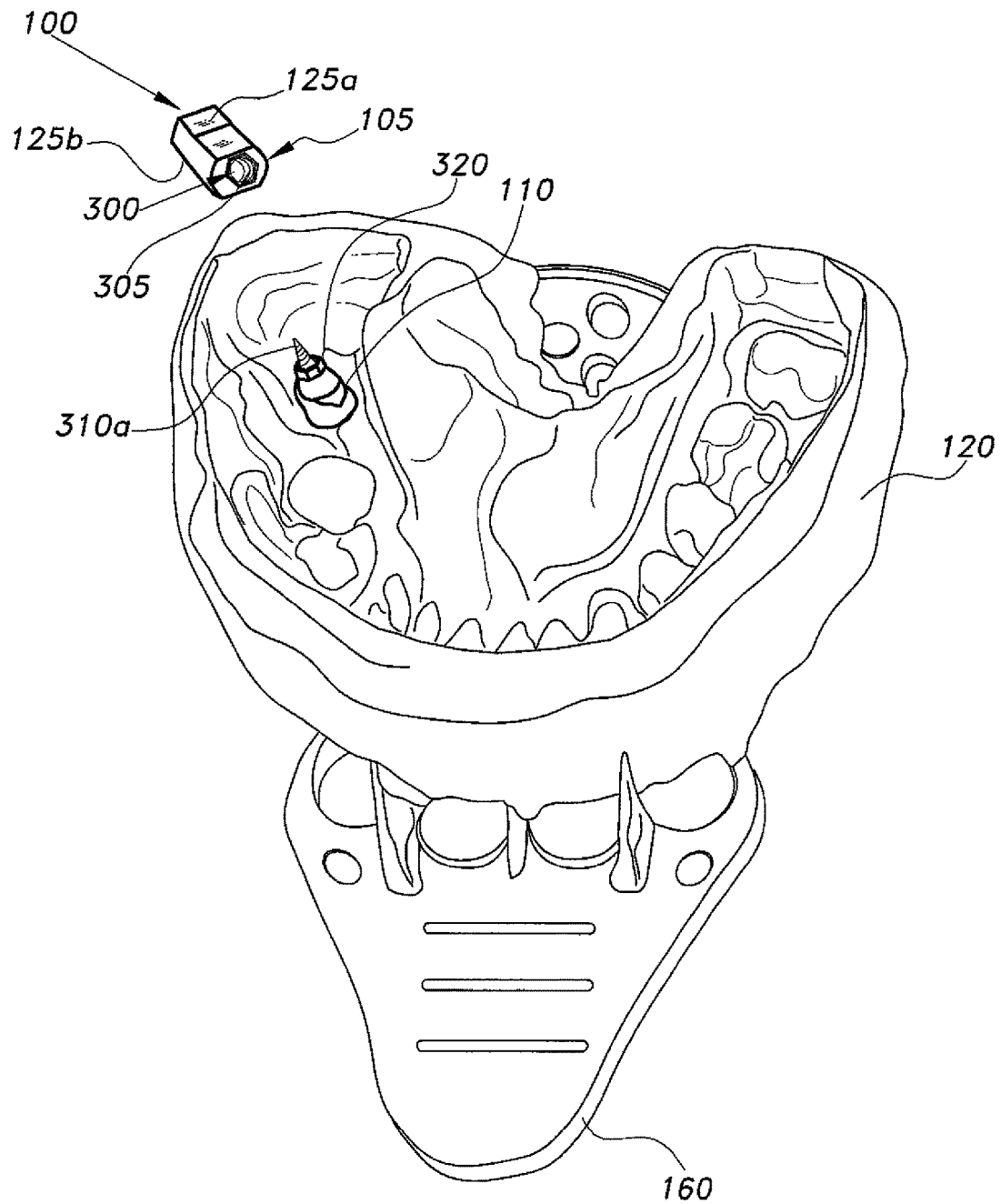
FIG. 3 is a front, perspective view of a dental impression having an impression coping including a fastener, according to the present invention.
Figure 4:
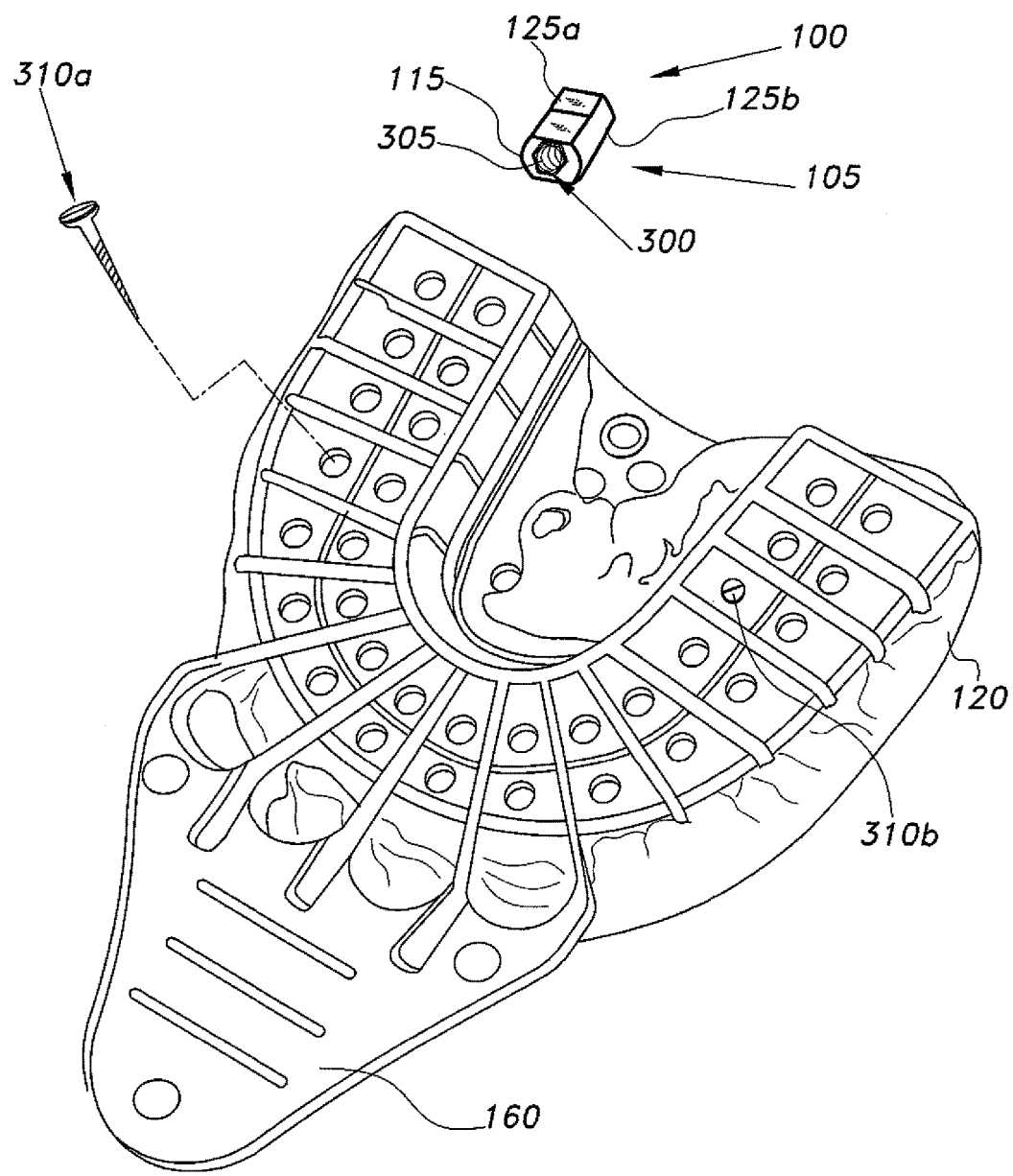
FIG. 4 is a bottom, perspective view a dental impression having a fastener, according to the present invention.
Figure 5A:
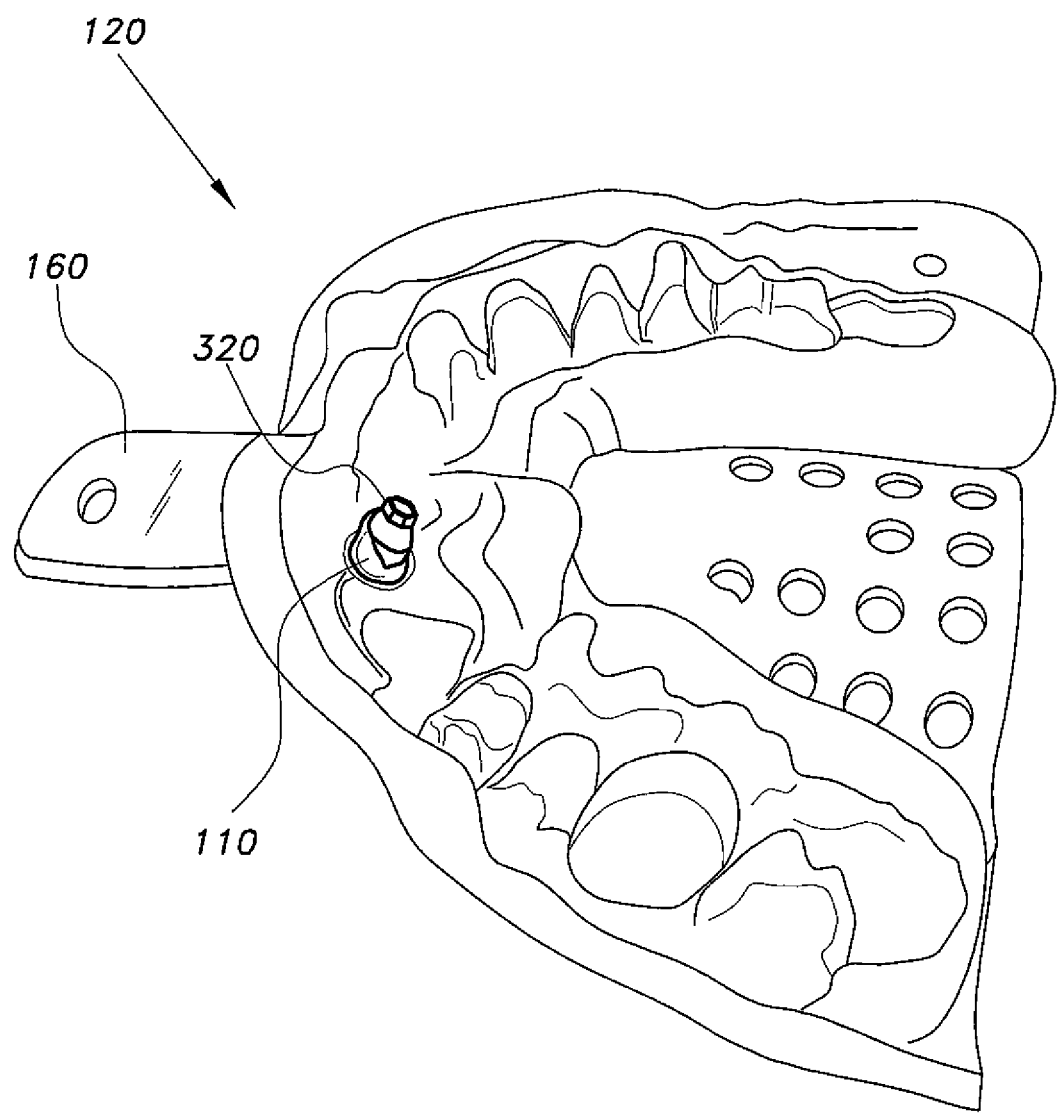
FIG. 5A is a side view of a dental impression having an impression coping including a head portion, according to the present invention.
Figure 5B:
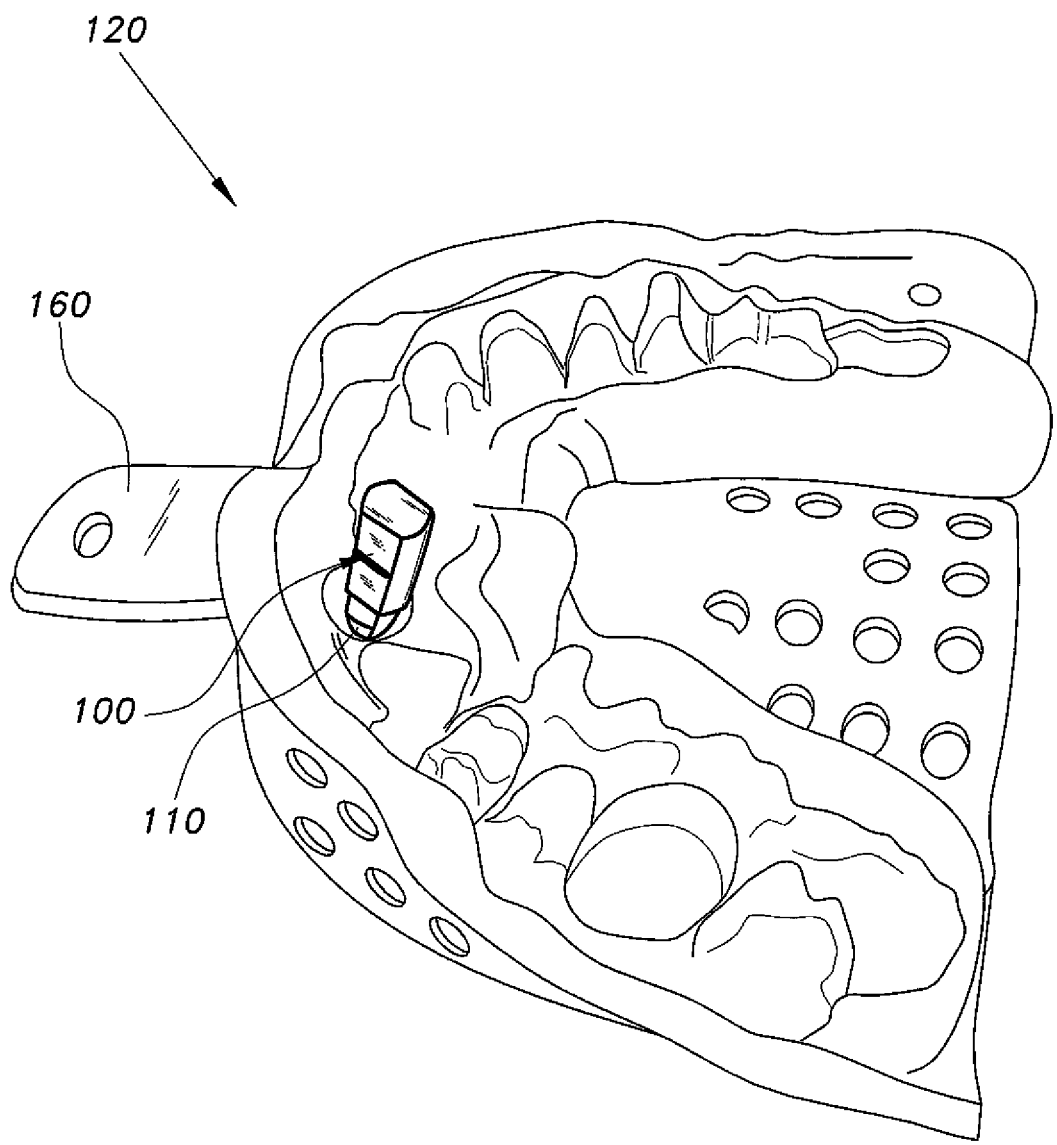
FIG. 5B is a side view of a scan body coupled to an impression coping positioned in a dental impression, according to the present invention.

Referring to FIGS. 1, 3, and 5B, a scan body 100 that can mate to an impression coping 110 inserted in a dental impression 120 of a patient's teeth is generally illustrated. The scan body 100 includes a hollow or substantially hollow member 105 having a mounting recess 300 defined therein. The scan body 100 is configured for mounting onto the impression coping 110 such as by engaging a head portion 320 of the impression coping 110 positioned in the dental impression 120. A fastener 310a can be inserted through the head portion 320 from a back side of the dental impression 120 (FIG. 4) such that the tip of the fastener 310a protrudes above the head portion 320. The mounting recess 300 can have an internal threaded bore 305 configured to receive the tip of the fastener 310a, such as a screw, to secure the scan body 100 onto the impression coping 110 positioned in the dental impression 120, as illustrated in FIGS. 1 and 5B. For example, once the scan body 100 is mounted onto the impression coping 110, the fastener 310a, can be inserted into the scan body 100 from the bottom, as illustrated in FIG. 4, to secure the scan body 100 thereto. The ability to secure the scan body 100 from the bottom can simplify securing the scan body 100 between adjacent existing teeth.

The hollow member 105 can have an exterior wall 115 (FIGS. 1 and 4) that is configured to allow Computer-Aided Design and Computer-Aided Manufacturing (CAD/CAM) technology to determine the orientation of the scan body 100 relative to the impression coping 110 in the dental impression 120. For example, the external wall 115 can include a first flat exterior surface 125a and a second flat exterior surface 125b. The first flat surface 125a can have a different length and/or height than the second flat surface 135. The positioning of the first flat exterior surface 125a and the second flat exterior surface 125b can then be used by the CAD/CAM system to determine the orientation of the scan body 100 relative to the impression coping 110.

The scan body 100 can have any suitable shape, such as a substantially rectangular, square, or cylindrical shape, and can be formed from any suitable medical grade material, such as titanium. The scan body 100 can be coated with any suitable coating, to make the exterior portion 115 of the scan body 100 opaque, which can make the scan body 100 capable of being scanned, by a scanner, such as a white light scanner. The fastener 310a can be made from any suitable medical grade material, such as titanium and can include a head 310 having any suitable type of configuration, such as a substantially circular configuration, as illustrated in FIG. 4.

The mounting recess 300 of the scan body 100 can have a hexagonal shape, as illustrated in FIGS. 3 and 4. The mounting recess 300 can receive the head portion 320, having a corresponding hexagonal shape.

By way of operation, after placing an implant (not shown) into the jaw bone of a patient's mouth, the dentist can insert the head portion 320 of the impression coping 110 into the opening of the implant. Once the impression coping 110 has been attached to the implant (positioned inside the patient's jaw bone) the impression coping 110 can be secured to the implant, such as by a thumb screw (not shown) inserted into the impression coping 110, which can then be tightened.

The dentist can then use impression material, such as Impregum™, to cover the patient's teeth and the impression coping 110 and an impression tray 160 to hold the impression material against the patient's teeth and the impression coping 110 until the impression material hardens so as to form the dental impression 120 of the patient's teeth. The impression material hardens to form the dental impression 120, as illustrated FIG. 5A. The dentist can remove the thumb screw attaching the impression coping 110 to the implant and, subsequently, remove the impression tray 160 including the hardened impression material and the impression coping 110 from the patient's mouth.

Figure 2A:
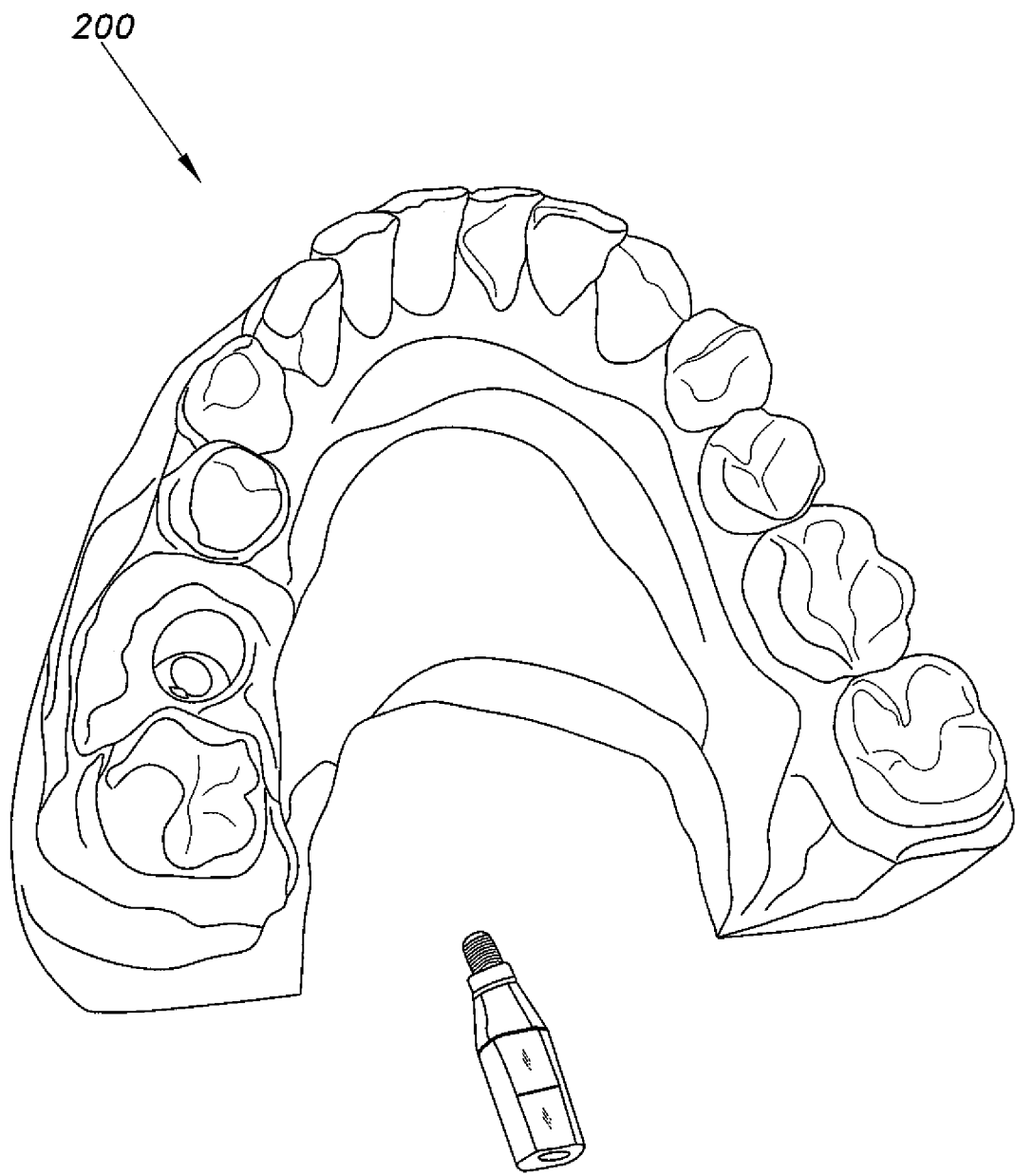
FIG. 2A is an environmental view of a dental mold and a scan body of the prior art.
Figure 2B:
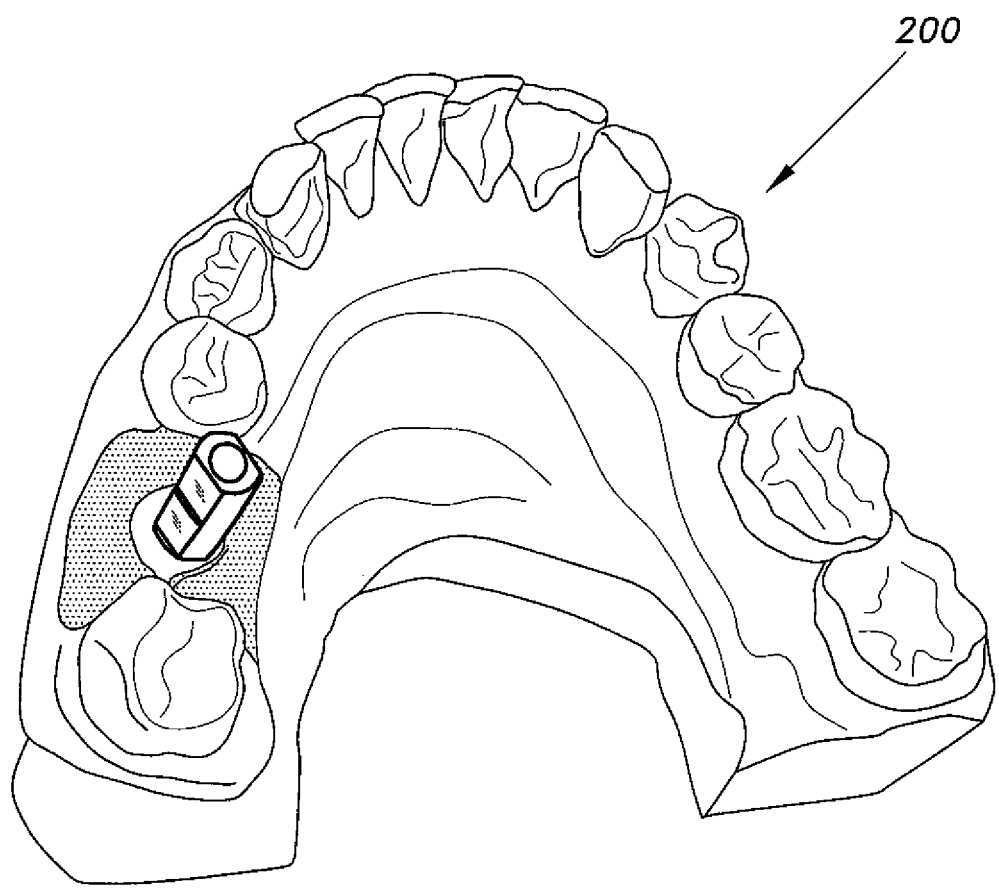
FIG. 2B is a perspective view of a dental mold having a scan body of the prior art.

Once the dental impression 120 having the impression coping 110 is removed from the patient's mouth, the scan body 100 can be attached to the head portion 320 of the impression coping 110, e.g., by inserting the head portion 320 into the mounting recess 300 of the scan body 100, as illustrated in FIGS. 1 and 5B. The dental impression 120 having the scan body 100 attached to the impression coping 110, as illustrated in FIGS. 1 and 5B, can then be scanned. The scanner, based on the orientation of the exterior wall 115 of the scan body 100 can determine the orientation and alignment of the scan body 100 in relation to the impression coping 110. This data can be transferred to the CAD/CAM system for use by a dentist and/or a lab technician to create a dental prosthesis (not shown), to replace broken or damaged tooth. Scanning the dental impression 120 and the scan body 100 directly, without having to make a dental mold 200 (FIGS. 2A and 2B), can decrease the number of steps required to create the dental prosthesis. As such, more accurate data and a faster and easier workflow can be achieved. Additionally, errors on the part of the dental lab when creating the dental prosthesis can be minimized.

It is to be understood that the present invention is not limited to the embodiments described above, but encompasses any and all embodiments within the scope of the following claims.

We claim:

1. A dental impression system, comprising:
a dental impression having an impression coping; and
a scan body consisting of a hollow member having a nonthreaded exterior peripheral wall extending between opposing first and second ends, the peripheral exterior wall having at least a first flat surface, wherein the first flat surface has an upper end, the upper end of the first flat surface being contiguous to the second end and extending towards the first end, the first end being open and in communication with a mounting recess configured for mounting onto the impression coping of the dental impression, the second end being closed.

2. The dental impression system according to claim 1, wherein the mounting recess comprises an internal threaded bore.

3. The dental impression system according to claim 1, further comprising a fastener.

4. The dental impression system according to claim 1, wherein the scan body is made from titanium.

5. The dental impression system according to claim 1, wherein the exterior peripheral wall includes a second flat surface, and a length and height of the first flat surface is different from a length and height of the second flat surface.

6. A method for creating a dental prosthesis from a dental impression, comprising the steps of:
(a) inserting an impression coping into an opening in an implant positioned in a patient's jaw bone;
(b) creating a dental impression of the patient's teeth including the impression coping;
(c) removing the dental impression from the patient's mouth;
(d) providing a scan body including a mounting recess defined therein, the scan body configured for mounting onto the impression coping positioned in the dental impression, the scan body consisting of a hollow member having a nonthreaded exterior peripheral wall extending between opposing first and second ends, the peripheral exterior wall having at least a first flat surface, wherein the first flat surface has an upper end, the upper end of the first flat surface being contiguous to the second end and extending towards the first end, the first end being open and in communication with a mounting recess configured for mounting onto the impression coping of the dental impression, the second end being closed, the exterior peripheral wall having a second flat surface, the first flat surface and the second flat surface having different dimensions;
(e) attaching the scan body onto the impression coping;
(f) scanning the dental impression having the scan body attached to the impression coping; and
(g) designing a prosthetic based on the information transferred by the scan of the dental impression having the scan body attached to the impression coping.

7. The method for creating a dental prosthesis from a dental impression according to claim 6, further comprising the step of securing the scan body to the impression coping.

8. The method for creating a prosthetic from a dental impression according to claim 6, wherein the mounting recess comprises an internal threaded bore.

9. The dental impression system according to claim 1, wherein the exterior peripheral wall has a second flat surface, the first flat surface and the second flat surface having different dimensions.

* * * * *